(12) United States Patent
Davies et al.

(10) Patent No.: US 6,779,216 B2
(45) Date of Patent: Aug. 24, 2004

(54) TOOTHBRUSH COVER

(75) Inventors: Richard Huw Davies, Gaggiano (IT); Anna Maini, Milan (IT); Luca Neri, Gaggiano (IT)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/183,791

(22) Filed: Jun. 27, 2002

(65) Prior Publication Data

US 2003/0000030 A1 Jan. 2, 2003

(30) Foreign Application Priority Data

Jun. 29, 2001 (EP) ............................................. 01305693

(51) Int. Cl.⁷ ............................ A46B 5/02; A46B 15/00
(52) U.S. Cl. ........................ 15/22.1; 15/143.1; D4/107; D4/113
(58) Field of Search .............................. 15/22.1, 143.1; D4/107, 113

(56) References Cited

U.S. PATENT DOCUMENTS

| | | | | |
|---|---|---|---|---|
| 1,380,633 A | * | 6/1921 | Brown | 40/314 |
| 2,016,644 A | * | 10/1935 | Abraham | 40/314 |
| 2,179,266 A | * | 11/1939 | Lukenbill | 15/145 |
| 2,620,500 A | * | 12/1952 | Ridner, Sr. | 15/184 |
| 2,814,818 A | * | 12/1957 | Birse | 15/143.1 |
| 4,438,300 A | | 3/1984 | Morse | |
| 5,126,572 A | * | 6/1992 | Chu | 250/455.11 |
| 5,309,591 A | | 5/1994 | Hagele et al. | |
| 5,383,091 A | | 1/1995 | Snell | |
| 5,848,152 A | | 12/1998 | Slipy et al. | |
| 5,982,881 A | | 11/1999 | Mischenko | |
| 6,015,328 A | * | 1/2000 | Glaser | 446/72 |
| 6,049,936 A | * | 4/2000 | Holley | 15/167.1 |
| 6,076,223 A | * | 6/2000 | Dair et al. | 15/167.1 |
| 6,422,867 B2 | * | 7/2002 | Lang et al. | 433/118 |

FOREIGN PATENT DOCUMENTS

| | | |
|---|---|---|
| DE | 196 39 197 | 9/1995 |
| EP | 0 683 995 | * 11/1995 |
| EP | 0 878 942 | 11/1998 |
| GB | 2 012 576 | 12/1978 |

\* cited by examiner

Primary Examiner—Randall Chin
(74) Attorney, Agent, or Firm—Milton L. Honig

(57) ABSTRACT

A method is provided for individualizing an electric toothbrush as well as a cover for a handle of a motorized toothbrush wherein the cover is firmly and removeably attacheable to the handle, characterized in that the toothbrush can be used with the cover in place.

8 Claims, 3 Drawing Sheets

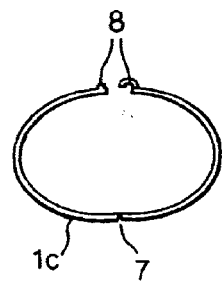
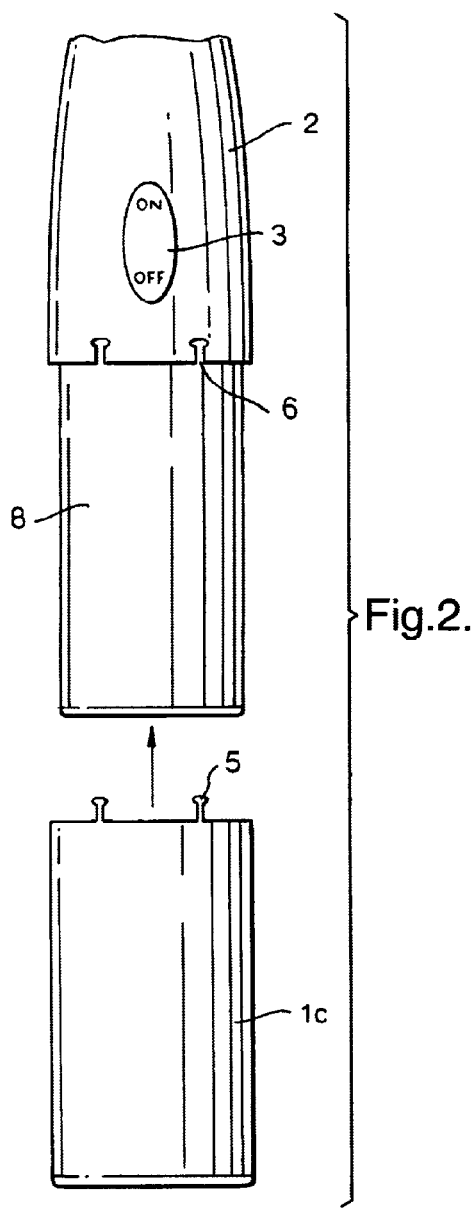
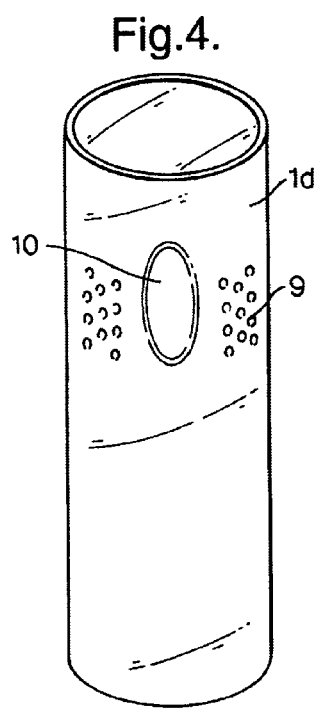

TOOTHBRUSH COVER

BACKGROUND OF THE INVENTION

1. Field of the Invention

This invention relates to electric toothbrushes. More particularly, the invention is concerned with functional covers that are removably attached to the handles of such brushes.

2. Related Art

Motorised toothbrushes typically comprise a handle section accommodating a motor, a power source, and a switch to control the motor. The motor then drives the brush head through a drive shaft or effects a vibration of the toothbrush head. The power source can either be mains electricity, a rechargeable power supply or disposable batteries in the case of an electric motor. Such motorised brushes are widely commercially available.

There are a number of problems with current motorised toothbrushes.

Many consumers now prefer to co-ordinate the colour schemes in their bathrooms, and would wish to have a toothbrush with a colour scheme matching their decor. However, while for manual toothbrushes a consumer is faced with a choice as to product colour or appearance, providing a suitable range of coloured electric toothbrushes would be prohibitively expensive and wasteful for the supplier as fashions dictate regular changes in colour schemes. Further, it is often the case that what is popular one minute may not be so a few months later. For example, a child may want a blue toothbrush one minute and a red one a few months later. If the child uses an electric toothbrush it would be expensive to purchase a new electric toothbrush just because the child wants one with a different colour.

There are also advantages in having a similar product with differing appearance since a family may comprise a larger number of individuals each wanting to use a similar type of electric toothbrush. It would thus be advantageous if each individual could purchase a product of a different colour to avoid using someone else's toothbrush. Accordingly, a manufacturer who could provide a large number of product formats which would appeal to a diverse consumer pool would benefit greatly since different people have different needs.

The current invention advantageously allows for the toothbrush user to easily change the cover themselves as they see fit. Therefore the particular colour scheme that the consumer wishes to have either for aesthetic or practical reasons can be met by removing the current cover and replacing this with a cover with the desired attributes.

Electric brushes are generally stored with the handle as a base, such that liquid from the used brush drains onto the handle, leading to the build up of deposits and necessitating regular cleaning of the handle. This means that the handles are generally made from shiny and non-tacky plastic which is easy to clean but difficult to grip.

When several people use the same bathroom, the need exists to identify which brushes belong to which owner for hygiene reasons. Some brushes are marked using coloured rings on the drive shaft of the brush, but these marks are easily masked by the build up of white toothpaste deposits over the rings.

GB 2,012,576 discloses a motorised toothbrush with a handgrip mounted on the housing. This handgrip acts as a moveable switch for brush head activity. In contrast to the current invention this handgrip is not detachable by the toothbrush user. A further limitation that GB 2,012,576 encompasses is the potential for build-up of toothpaste and other deposits such as microbial contamination inadvertently caught between the moving parts. This could occur because as the hand-grip portion moves between two extreme positions of movement, gaps are created between the hand-grip and the housing. Likewise this design leads to the potential for the pinching of fingers between such moveable parts. The current invention overcomes these problems by disclosing a cover that can be easily removed so that cleaning of both the cover and the handle can be carried out separately by the toothbrush user. This removes the need to attempt to clean the hard to reach places between the moveable parts in GB 2,012,576. The cover in this invention is also firmly attached to the handle so that in use it does not move in such a way that could pinch a finger or get build up of deposits taking place. U.S. Pat. No. 5,309,591 discloses a protective cover for such a motorised brush, adapted to prevent the brush from being switched on when transported. However, this also requires that the cover is removed before brushing can take place.

SUMMARY OF THE INVENTION

The current invention overcomes the problems of the prior art by providing a cover for a handle of a motorised toothbrush wherein the cover is firmly and removeably attachable to the handle by the toothbrush user, characterised in that the toothbrush can be used with the cover in place.

The toothbrush must be capable of being used when the cover is in place. Since the invention relates to motorised electric toothbrushes it is meant that the cover may be attached to the brush handle and maintained there without having to be removed to actuate the electric elements of the brush. In such a way the cover may be placed on the handle and then left there for the lifetime of the brush or even until another cover is to be employed. This is contrast to the device according to the prior art which must be removed to actuate the brush but which, in theory, could be reattached after the brush has been turned on and then used during brushing.

BRIEF DESCRIPTION OF THE DRAWINGS

Further features and advantages of the invention will become more apparent through consideration of the drawings in which:

FIG. 1b is a perspective view of a cover for the handle in FIG. 1a;

FIG. 2 is a plan view of a cover and handle;

FIG. 3 is an end on view of an alternative cover;

FIG. 4 is a perspective view of an alternative cover;

DETAILED DESCRIPTION OF THE INVENTION

Figure 1A:
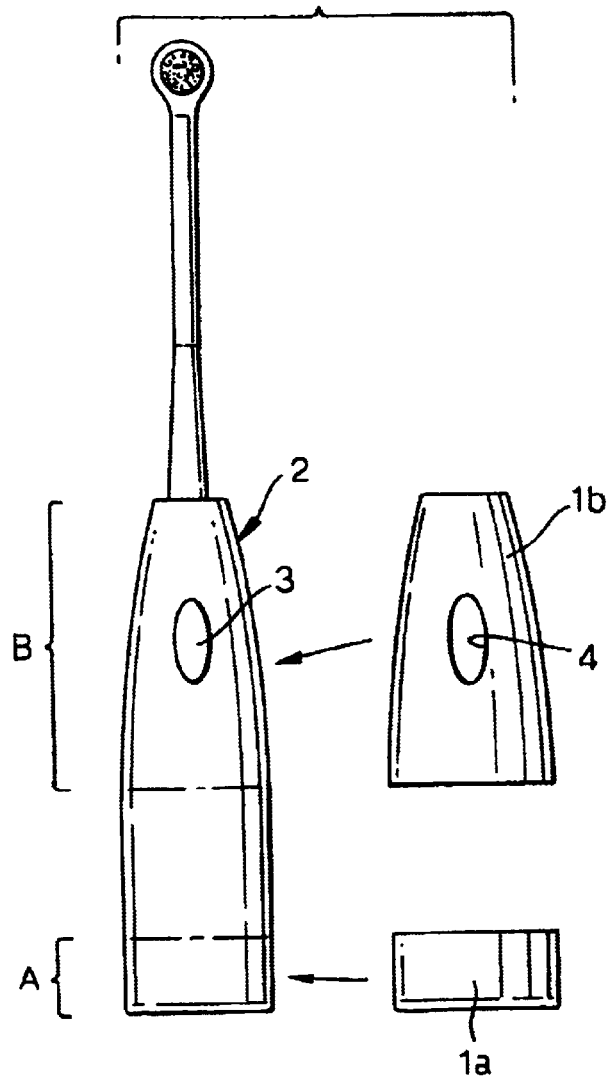
FIG. 1a is a plan view of a first embodiment.

The cover can be made as a relatively simple moulding, allowing manufacture in a variety of fashionable colours at much lower cost to the manufacturer than the complex handle moulding. Because the cover can be removed for thorough cleaning, it can be made from an elastomeric or tacky plastic or provided with protruberences in order to improve the grip of the user on the handle in use. Such thorough cleaning without a removable cover might lead to ingress of water and damage to the moving parts of the motorised toothbrush. The cover can also be of a large surface area so that it prominently identifies the ownership of the brush.

The cover for the brush may take any shape and form. However, the cover will always allow for the brush to be used when it is fixed to the handle. The means to allow operation of a control switch on the handle when the cover is in place can be any physical manifestation. For example, it may take the form of an orifice in the cover such that a switch on the handle may be operated. The means may also be a weakening in the cover such that the cover overlying the switch may be deformed to allow for operation of said switch. Typically, such a weakening may comprise a resilient material, e.g. a rubber or elastomer or even a thin portion of the cover itself.

The handle of the motorised toothbrush typically houses the motor and is usually elongate and conical in shape with a flat base for standing the brush upright at its base and a drive-connecting means for connecting to the brush head at the opposite end.

The cover according to the invention is intended to cover at least a portion of the brush handle such that the appearance of the handle may be changed as a result of the outer surface of the cover. For example, a handle of the brush may be plain white (electric toothbrushes are often categorised as 'white goods' commercially) and the cover would be sufficiently sized so as to provide a distinguishing appearance. This cover may actually comprise a geometric shape, e.g. a star or square etc. so long as it is capable of being removeably attachable to a handle of an electric toothbrush. Preferably, the cover is of significant proportion with respect to the handle of the brush, i.e. it covers at least a portion of the outer surface of said handle.

In principle the cover of the invention can be attached to any electric toothbrush providing that it is attachable to it. For example, the cover may be in the from of a strap which surrounds a longitudinal portion of the handle of the brush. In this way it is capable of distinguishing the brush of one user from another brush, e.g. by way of its colour.

Preferably, the attachment between the cover and the handle is of such a nature that the cover is secured in a fixed position on the handle. Also, the cover and handle comprise co-operating locking means so that attachment is more secure. Such co-operating locking means may be a click-fit, snap-fit or any other releasable attachment mechanism. The handle typically comprises means to facilitate such fixing, for example, the handle may comprise a longitudinal groove which allows fixing of a cover by a clasping engagement. The handle may also be specifically designed to correspond with a particular type of cover. For example the handle may actually be incomplete without any cover attached, the handle comprising a recess which needs to be accommodated by a corresponding cover which, of course, may be changed at any time.

The cover may also be in more than one individual part with said more than one part being co-operated upon fixing to the handle.

The cover is usually made from any material typically used in toothbrush manufacture, e.g. polypropylene and polyacrylonitrile to name just two. Suitably, it is made from the same material as the handle of the electric brush although it may employ another material to achieve better gripping during use when the device is wet. An elastomeric material may be used should a softer material be desired. Preferably, the cover comprises a polypropylene material with elastomeric material being used to improve gripping during use.

The cover of the invention is attachable to the handle of an electric toothbrush such that the latter can be activated when the cover is attached. This is in contrast to the devices of the prior art which have as their object a device which cannot be activated when the cover is in place.

This can be achieved by a cover, which has a window in its structure allowing an activator switch on the handle to be depressed. This can also be achieved by a cover, which does not cover the activating switch or even cover any of the surrounding handle area.

Such a window in the cover may actually be a blind window, by which is meant that there is no actual aperture or orifice but a more flexible area through which the switch can be activated.

The cover according to the invention may also be used to present information about a product for a different commercial market. For example, the cover may incorporate a trade mark for one particular commercial market while another otherwise identical cover may show a different trade mark or instructions in a different language even though the actual brush is the same. In this way a single brush can be made without having to incorporate different market requirements into the manufacturing chain.

Embodiments according to the invention will now be considered with reference to the following drawings in which FIGS. 1 to 6 show different covers according to the invention.

Figure 1B:
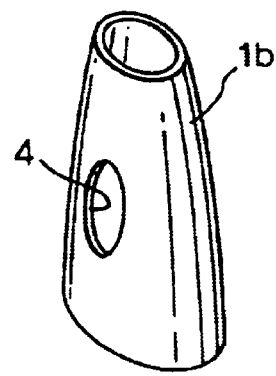
Figure 1C:
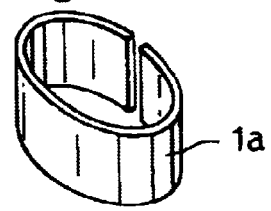
FIG. 1c is a perspective view of an alternative cover.

FIG. 1 discloses an upper shroud (1a) and a lower shroud (1b) which are reversibly attachable to a handle (2) of an electric toothbrush.

Upper shroud (1a) is a cover of short longitudinal length only covering the base portion (A) of the handle (2) of the brush. In any case it is capable of distinguishing the brush from another with a different cover or a similar cover of different colour.

Lower shroud (1b) is another cover and covers a portion (B) of the brush handle (2) which also includes an activating switch (3). The shroud (1b) is thus capable of being attached to the handle (2) and by way of an aperture (4) which corresponds to the size of the switch (3) the brush can be used while the cover is attached.

Both shrouds (1a and 1b) are attached to the handle by resilient attachment in that they are flexed so that they can be slidingly and telescopically engaged with the handle.

FIG. 2 discloses a brush handle (2) with an activating switch (3) and a cover (1c) which can be slid along the outer surface of an area of the handle (2) which forms a recess (8) conforming to the dimensions of the cover (1c) such that the cover (1c) and handle (2) provide a flush surface relative to one another. The cover (1c) in this case is attached to the handle by way of co-operating locking means in the form of pegs (5) and notches (6).

FIG. 3 is an end on view of a cover which is in the form of two interlocking parts which can be engaged on fixing to the handle or dis-engaged when the cover is to be removed from the handle. The two parts are linked by a hinge (7) and the locking means can be any locking means common in the art but in this case are in the form of a latch (8).

FIG. 4 is a cover according to the invention which is in the form of a resilient sheath which can be stretched over the handle of the brush. The sheath is, of course, capable of displaying different graphics or can be coloured. The sheath in this example can be made from any suitably resilient material such as an elastomeric material. This particular cover also comprises purchasing means (9), such as a surface which is roughened or comprises regular or irregular projections, etc. for improving the grip during use and a recess (10) for corresponding with an activation switch on the handle of the brush.

Figure 5:
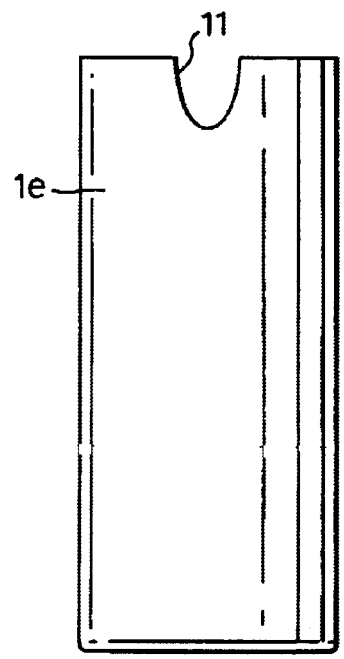
FIG. 5 is a plan view of yet a further embodiment of the invention.

FIG. 5 shows a cover (1e) which is capable of covering a substantial area of the brush handle and also covers a proportion of the area around an activation switch on the handle. It comprises an inner bight (11) which corresponds with the shape of the activation switch.

Figure 6:
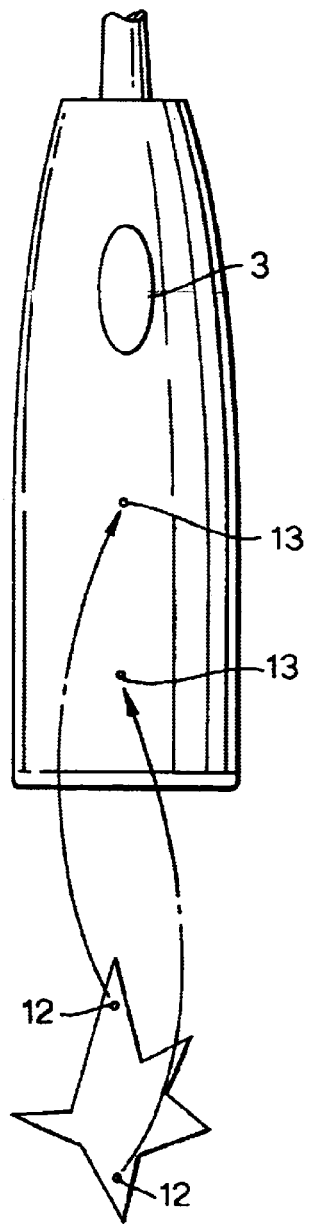
FIG. 6 is still a further embodiment of a cover according to the invention.
Figure 6A:
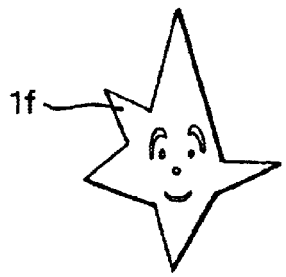
FIG. 6a is a star-shaped caricature used with the embodiment described in FIG. 6.

FIG. 6 shows a cover (1f) in the form of a star-shaped caricature figure which can be reversibly attached to the handle of a brush. It comprises fixing means in the form of pegs (12) which can engage with corresponding notches (13) on a handle (2). Further suitably useful fixing means include a snap-fit mechanism, a magnet or even a ratchet.

What is claimed is:

1. A method for individualising an electric toothbrush comprising:
   (a) providing an electric toothbrush comprising:
      (i) a brush handle;
      (ii) an electric motor activatable by a switch, the motor and switch housed within the handle;
      (iii) a brush head attached to the handle and vibratable through communication with the motor; and
      (iv) a shroud removably attachable as a cover over at least one portion of the brush handle, the brush head being vibratable with the shroud attached over the at least one portion of the brush handle, the cover being furnished with a means to allow operation of a control switch on the handle when the cover is attached to the handle;
   (b) removing the shroud and replacing with an alternative shroud.

2. A method as claimed in claim 1, wherein the cover and handle are furnished with co-operating locking means to hold the cover in a fixed position on the handle.

3. A method as claimed in claim 1, wherein the cover is formed from at least two interlocking parts.

4. A method as claimed in claim 1, wherein the cover is formed of a hard plastic material.

5. A method as claimed in claim 1, wherein the cover is formed from an elastomeric material.

6. A method as claimed in claim 1, wherein the means to allow the operation of the control switch is an opening through the cover.

7. A method as claimed in claim 1, wherein the cover is provided with an external surface adapted to aid gripping.

8. A method as claimed in claim 1, wherein the cover is adapted to allow a personalised message to be displayed on the cover.

* * * * *